(12) United States Patent
Ishibashi et al.

(10) Patent No.: US 9,822,050 B2
(45) Date of Patent: Nov. 21, 2017

(54) TERMINAL CONJUGATED TRIENAL ACETAL COMPOUND AND METHOD FOR PRODUCING TERMINAL CONJUGATED TRIENAL COMPOUND USING THE SAME

(71) Applicant: Shin-Etsu Chemical Co., Ltd., Chiyoda-ku, Tokyo (JP)

(72) Inventors: Naoki Ishibashi, Joetsu (JP); Shinnosuke Wakamori, Joetsu (JP); Yuki Miyake, Joetsu (JP); Miyoshi Yamashita, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/447,817

(22) Filed: Mar. 2, 2017

(65) Prior Publication Data

US 2017/0253548 A1 Sep. 7, 2017

(30) Foreign Application Priority Data

Mar. 3, 2016 (JP) ................................ 2016-041069

(51) Int. Cl.
 C07C 45/00 (2006.01)
 C07C 43/303 (2006.01)
 C07C 41/54 (2006.01)

(52) U.S. Cl.
 CPC .......... *C07C 43/303* (2013.01); *C07C 41/54* (2013.01); *C07C 45/00* (2013.01); *C07B 2200/09* (2013.01)

(58) Field of Classification Search
 None
 See application file for complete search history.

(56) References Cited

PUBLICATIONS

T. C. Baker et al., "Isolation, Identification and Synthesis of Sex Pheromone Compnents of the Carob Moth, *Ectomyelois ceratoniae*," Tetrahedron Letters, 1989, pp. 2901-2902, vol. 30, No. 22, Pergamon Press plc, Great Britain.
P. Zagatti et al., "Sex Pheromone of *Stenoma cecropia* Meyrick (Lepidoptera: Elachistidae)," Journal of Chemical Ecology, 1996, vol. 22, No. 6, pp. 1103-1121, Plenum Publishing Corporation.
F. Tellier et al., "Stereospecific Synthesis of (Z,E)-9,11,13-Tetradecatrien-1-YL Acetate and Aldehyde Sex Pheromone Compnents of Stenoma Cecropia and Ectomyelois Ceratoniae," Tetrahedron Letters, 1990, pp. 2295-2298, vol. 31, No. 16, Pergamon Press plc, Great Britain.
J.A. Cabezas-Pizarro et al., "An Improved Stereospecific Synthesis of (Z,E)-9,11-13-tetradecatrienal. Sex Pheromone Component of Stenoma Cecropia," Ingenieria y Ciencia Quimica, 2000, pp. 55-58, vol. 19, No. 2 (one (1) page).

*Primary Examiner* — Clinton Brooks
*Assistant Examiner* — Ana Z Muresan
(74) *Attorney, Agent, or Firm* — Crowell & Moring LLP

(57) ABSTRACT

Provided are a terminal conjugated trienal acetal compound useful as an intermediate for producing a terminal conjugated trienal compound, and a method for producing a terminal conjugated trienal compound through deprotection of the terminal conjugated trienal acetal compound. More specifically, provided are a terminal conjugated trienal acetal compound represented by General Formula (1); a method for producing a (Z,E)-terminal conjugated trienal acetal compound, the method comprising the step of: reacting a phosphonium salt represented by General Formula (7) with (E)-2,4-pentadienal through Wittig reaction to obtain a (Z,E)-terminal conjugated trienal acetal compound represented by General Formula (3); and a method for producing a terminal conjugated trienal compound, the method comprising the step of: deprotecting the terminal conjugated trienal acetal compound represented by General Formula (1) to obtain a terminal conjugated trienal compound represented by General Formula (2).

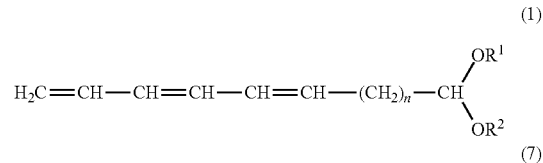

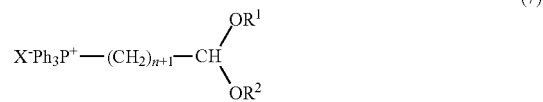

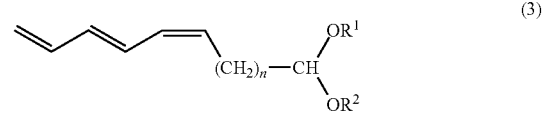

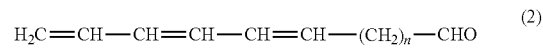

6 Claims, No Drawings

TERMINAL CONJUGATED TRIENAL ACETAL COMPOUND AND METHOD FOR PRODUCING TERMINAL CONJUGATED TRIENAL COMPOUND USING THE SAME

BACKGROUND OF THE INVENTION

1. Field of the Invention

The present invention relates to a terminal conjugated trienal acetal compound useful as an intermediate for synthesis of an insect sex pheromone and to a method for producing a terminal conjugated trienal compound through deprotection of the terminal conjugated trienal acetal compound.

2. Description of the Related Art

Insect sex pheromones are the biologically active substances which are commonly secreted by female insects and have the function of attracting male insects. A small amount of a sex pheromone shows strong attractive activities. Sex pheromones have been widely used as means for forecasting insect emergence or for ascertaining regional spread (invasion into a specific region) and as means for controlling insect pests. As the means for controlling insect pests, control methods such as mass trapping, lure-and-kill or attract-and-kill, lure-and-infect or attract-and-infect, and mating disruption are widely used in practice. To utilize a sex pheromone, economical production of a required amount of pheromone product is required for basic research and also for application.

Ectomyelois ceratoniae (generic name: Carob moth), which is widely spread in the world and is polyphagous, damages various crops such as nuts and fruits, and thus is an economically serious insect pest. Baker et al. extracted the pheromone glands of Carob moth and found that the sex pheromone thereof was a mixture of (Z,E)-9,11,13-tetradecatrienal, (Z,E)-9,11-tetradecadienal and (Z)-9-tetradecenal at 8:1:1 (Tetrahedron Lett., 30, 2901 (1989)). They synthesized (Z,E)-9,11,13-tetradecatrienal by the method comprising the steps of: Wittig reaction of (E)-2,4-pentadienylidenetriphenylphosphorane with 9-t-butyldimethylsilyloxynonanal, separation of geometric isomers by HPLC, deprotection, and oxidation of a hydroxy group, and confirmed that the above identification had been correct.

Zagatti et al. report that the main component of the sex pheromone of Stenoma cecropia, which is an insect pest causing serious damage to oil palm farms in Colombia, is the same (Z,E)-9,11,13-tetradecatrienal as that of Carob moth (J. Chem. Ecol., 22, 1103 (1996)).

As the other methods for producing (Z,E)-9,11,13-tetradecatrienal, the following two examples are known.

The method of Tellier et al. comprises the steps of: coupling between 10-t-butoxy-1-decyne and 1,2-dibromoethylene, vinylation with a vinyl zinc reagent, reduction of the resulting conjugated dienyne with metallic zinc, deprotection, and oxidation of a hydroxy group (Tetrahedron Lett., 31, 2295 (1990)).

The method of Cabezas et al. comprises the steps of: reduction of the same conjugated dienyne as that in the method of Tellier et al. by hydroboration-protonolysis, deprotection, and oxidation of a hydroxy group (Ingenieria y Ciencia Quimica, 19 (2), 55, (2000)).

SUMMARY OF THE INVENTION

The method of Baker et al. comprises the step of Wittig reaction of (E)-2,4-pentadienylidenetriphenylphosphorane, which is a metastable ylide stabilized by conjugation, and thus is expected to give low Z-selectivity (no results are reported). The method of Baker et al. also comprises the step of a reaction such as ozone oxidation or oxidation of a hydroxy group, which is difficult to be carried out industrially. The method of Tellier et al. comprises two steps of using an expensive palladium catalyst, and involves large excess amounts of 1,2-dibromoethylene, a vinyl zinc reagent and an activated metallic zinc, thereby providing economic disadvantages. The method of Tellier et al. also involves, as the oxidizing agent for a hydroxy group, pyridinium dichromate (PDC), which generates poisonous chromium waste products, and thus is difficult to be carried out industrially. The method of Cabezas et al. comprises substantially the same steps as those in the method of Tellier et al. except that the conjugated dienyne was reduced by hydroboration-protonolysis. Thus, the method of Cabezas et al. results in economic disadvantages and is difficult to be carried out industrially.

When formation of an aldehyde moiety is focused, the aldehyde is formed by oxidation of a hydroxy group in all of the above three examples. The oxidation needs deprotection of a protected hydroxy group before the oxidation so that two steps of the deprotection and the oxidation are required. On the other hand, when an aldehyde protection compound is used as a precursor, the aldehyde moiety can be formed only in one step of deprotection. A typical aldehyde protection compound includes an acetal compound. However, since a terminal conjugated triene structure is extremely unstable, the acetal compound, which requires an acidic condition for deprotection, has not been used as the precursor of the terminal conjugated trienal compound.

For the purposes of basic biological studies and agronomic studies of sex pheromones of Carob moth and Stenoma cecropia as well as the purposes of application and practical use thereof, there is a strong demand for an efficient and selective method for producing (Z,E)-9,11,13-tetradecatrienal capable of supplying sufficient amounts of the pheromone product.

The present invention has been completed under the above circumstances. In the present invention, a terminal conjugated trienal acetal compound useful as an intermediate for producing a terminal conjugated trienal compound and a method for producing a terminal conjugated trienal compound through deprotection of the trienal acetal compound are provided.

The present inventors have carried out intensive studies in order to achieve the object. As a result, they have unexpectedly found that a terminal conjugated trienal compound can be efficiently produced through deprotection of a terminal conjugated trienal acetal compound without disruption of the terminal conjugated triene structure, and have completed the present invention.

In an embodiment of the present invention, provided is a terminal conjugated trienal acetal compound represented by General Formula (1)

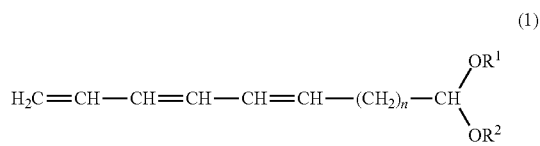

where n is an integer of 2 to 11; and each of $R^1$ and $R^2$ independently represents a monovalent hydrocarbon group having 1 to 10 carbon atoms, or $R^1$ and $R^2$ are bonded to each other to form a divalent hydrocarbon group having 2 to 10 carbon atoms as $R^1$-$R^2$.

In another embodiment of the present invention, provided is a method for producing a (Z,E)-terminal conjugated trienal acetal compound, the method comprising the step of: reacting a phosphonium salt represented by General Formula (7):

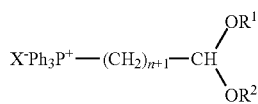
(7)

wherein n is an integer of 2 to 11; each of $R^1$ and $R^2$ independently represents a monovalent hydrocarbon group having 1 to 10 carbon atoms, or $R^1$ and $R^2$ are bonded to each other to form a divalent hydrocarbon group having 2 to 10 carbon atoms as $R^1$-$R^2$; and X is a halogen atom, with (E)-2,4-pentadienal through a Wittig reaction to obtain a (Z,E)-terminal conjugated trienal acetal compound represented by General Formula (3):

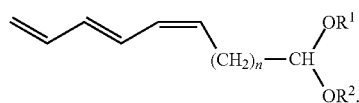
(3)

In an embodiment of the present invention, provided is a method for producing a terminal conjugated trienal compound, the method comprising the step of: deprotecting the terminal conjugated trienal acetal compound represented by General Formula (1) to obtain a terminal conjugated trienal compound represented by General Formula (2):

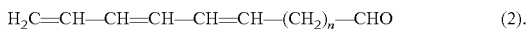
(2).

According to the present invention, a terminal conjugated trienal compound can be efficiently produced through deprotection of a terminal conjugated trienal acetal compound without disruption of the unstable terminal conjugated triene structure. No change in the ratio of geometric isomers is observed before and after the deprotection. Accordingly, when a (Z,E)-terminal conjugated trienal acetal compound is selectively produced, for example, by using Wittig reaction with (E)-2,4-pentadienal, the (Z,E)-terminal conjugated trienal acetal compound may be subjected to deprotection to efficiently produce a (Z,E)-terminal conjugated trienal compound. As a result, for example, (Z,E)-9,11,13-tetradecatrienal, which is the main component of sex pheromones of Carob moth and Stenoma cecropia, can be efficiently produced.

DETAILED DESCRIPTION OF THE PREFERRED EMBODIMENTS

Embodiments of the present invention will now be described in detail. It should not be construed that the invention is limited to or by them.

The chemical formulae of intermediates, reagents and target compounds in the present specification can include isomers different in substitution sites and stereoisomers such as enantiomers and diastereomers in terms of structure. Unless otherwise stated, each chemical formula is intended to represent all the isomers in each case. The isomer may be used alone or as a mixture of two or more.

[I] Terminal Conjugated Trienal Acetal Compound (1)

In the present invention, a terminal conjugated trienal acetal compound represented by General Formula (1) below is provided.

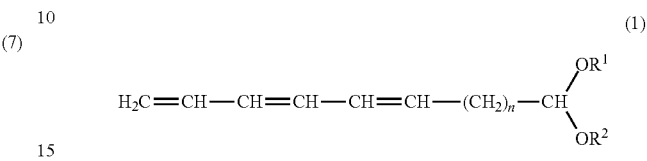
(1)

The "n" is an integer of 2 to 11; and each of $R^1$ and $R^2$ independently represents a monovalent hydrocarbon group having 1 to 10 carbon atoms, or $R^1$ and $R^2$ are bonded to each other to form a divalent hydrocarbon group having 2 to 10 carbon atoms as $R^1$-$R^2$.

Examples of the monovalent hydrocarbon group include monovalent hydrocarbon groups having 1 to 10 carbon atoms, preferably 1 to 5 carbon atoms. Examples of the monovalent hydrocarbon group include a linear or branched, saturated monovalent hydrocarbon group such as a methyl group, an ethyl group, an n-propyl group, an n-butyl group, an n-pentyl group and an isopropyl group; a linear or branched, unsaturated monovalent hydrocarbon group such as a 2-propenyl group, a 2-methyl-2-propenyl group and a 2-propynyl group; and a cyclic hydrocarbon group such as a cyclopropyl group, a 2-methylcyclopropyl group, a cyclobutyl group and a cyclopentyl group; and also include monovalent hydrocarbon groups that are isomers of them. One or more hydrogen atoms of such a monovalent hydrocarbon group may be replaced, for example, by a methyl group or an ethyl group. Of these monovalent hydrocarbon groups, lower monovalent hydrocarbon groups having 1 to 4 carbon atoms and primary monovalent hydrocarbon groups are preferred in consideration of the reactivity of the deprotection and easy purification. It is because they have high reactivity and by-products formed by deprotection can be easily removed by water washing or concentration. Further considering the above, particularly preferred examples of $R^1$ and $R^2$ include a methyl group, an ethyl group and an n-propyl group.

When each of $R^1$ and $R^2$ independently represents a monovalent hydrocarbon group having 1 to 10 carbon atoms, $R^1$ and $R^2$ are preferably the same from the standpoint of convenience of synthesis and purification.

Next, the case in which $R^1$ and $R^2$ are bonded to each other to form a divalent hydrocarbon group having 2 to 10 carbon atoms as $R^1$-$R^2$ will be described.

Examples of the divalent hydrocarbon group include divalent hydrocarbon groups having 2 to 10 carbon atoms, preferably 2 to 6 carbon atoms. Examples of the divalent hydrocarbon group include a linear or branched, saturated hydrocarbon group such as an ethylene group, a 1,2-propylene group, a 1,3-propylene group, a 2,2-dimethyl-1,3-propylene group, a 1,2-butylene group, a 1,3-butylene group, a 1,4-butylene group, a 2,3-butylene group and a 2,3-dimethyl-2,3-butylene group; a linear or branched, unsaturated hydrocarbon group such as a 1-vinylethylene group, a 2-methylene-1,3-propylene group and a (Z)-2-butene-1,4-diyl group; and a cyclic hydrocarbon group such as a 1,2-cyclopropylene group, a 1,2-cyclobutylene group, a 1,2-cyclopentylene group, a 1,2-cyclohexylene group and a 1,2-phenylene group; and also include hydrocarbon groups that are isomers of them. One or more hydrogen atoms of such a divalent hydrocarbon group may be replaced, for example, by a methyl group or an ethyl group. Of these divalent hydrocarbon groups, particularly preferred examples include an ethylene group, a 1,2-propylene group, a 1,3-propylene group, a 1,2-butylene group, a 1,3-butylene group and a 2,3-dimethyl-2,3-butylene group in consideration of the reactivity of the deprotection, easy purification and easy availability.

[II] Method for Producing Terminal Conjugated Trienal Acetal Compound

The terminal conjugated trienal acetal compound represented by General Formula (1) can include four types of geometric isomers. One of them is a (Z,E)-terminal conjugated trienal acetal compound represented by General Formula (3).

The (Z,E)-terminal conjugated trienal acetal compound can be synthesized efficiently and selectively by using a Wittig reaction of a phosphonium salt represented by General Formula (7) with (E)-2,4-pentadienal. In the general formulae below, the definitions of n, $R^1$, and $R^2$ are the same as above; and X represents a halogen atom and is preferably a chlorine atom, a bromine atom or an iodine atom.

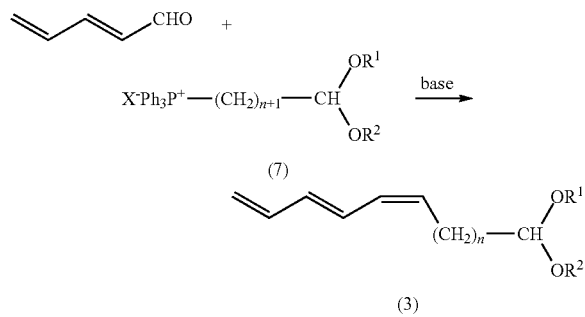

The phosphonium salt represented by General Formula (7) can be produced by reacting a halide represented by General Formula (8) below with triphenylphosphine in a solvent. In General Formula (8), the definitions of n, $R^1$, $R^2$ and X are the same as above.

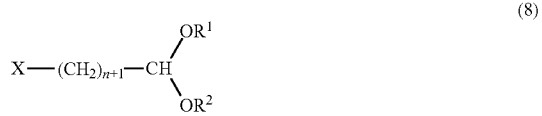

When the halide represented by General Formula (8) is reacted with triphenylphosphine in a solvent to obtain a phosphonium salt, a metal halide and/or a quaternary onium salt may be added to accelerate the reaction. Examples of the metal halide include lithium iodide, sodium iodide, potassium iodide, lithium bromide, sodium bromide and potassium bromide. Examples of the quaternary onium salt include tetraethylammonium bromide, tetrabutylammonium bromide, tetrabutylphosphonium bromide, tetraethylammonium iodide, tetrabutylammonium iodide and tetrabutylphosphonium iodide.

As for preparation of the phosphonium salt, a hydrogen carbonate such as lithium hydrogen carbonate, sodium hydrogen carbonate and potassium hydrogen carbonate; a carbonate such as lithium carbonate, sodium carbonate and potassium carbonate; a hydroxide such as lithium hydroxide, sodium hydroxide and potassium hydroxide; or an organic base such as triethylamine, diisopropylethylamine, tributylamine, N,N-dimethylaniline, N,N-diethylaniline, pyridine, 4-dimethylaminopyridine, quinoline, pyrrolidine, piperidine, collidine, lutidine and morpholine may be added to make the reaction solution basic during the preparation of the phosphonium salt.

Examples of the solvent for preparing the phosphonium salt may include the same solvent as for the Wittig reaction described later, and the amount of the solvent is preferably 10 g to 10,000 g relative to 1 mol of the halide.

The reaction temperature for preparing the phosphonium salt varies depending on reaction conditions. The reaction temperature may be −10° C. to 180° C., preferably 0° C. to 160° C., more preferably 10° C. to 140° C.

The reaction time for preparing the phosphonium salt may be freely selected. The reaction time is preferably selected to complete the reaction by monitoring the reaction by gas chromatography (GC) or silica gel thin-layer chromatography (TLC) from the standpoint of yield. The reaction time is typically about 0.5 to about 60 hours.

The (E)-2,4-pentadienal, which will be subjected to a Wittig reaction with the phosphonium salt thus prepared, may be a commercial product or a compound prepared by a known method. The amount of (E)-2,4-pentadienal may be 0.6 to 5 mol, preferably 0.7 to 4 mol, more preferably 0.8 to 3 mol relative to 1 mol of the phosphonium salt.

Examples of the base to be used for the Wittig reaction include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide and potassium t-amyloxide; organometallic reagents such as methyllithium, ethyllithium, n-butyllithium, methylmagnesium chloride and dimsyl sodium; metal amides such as sodium amide, lithium amide, lithium diisopropylamide, lithium hexamethyldisilazide, sodium hexamethyldisilazide, potassium hexamethyldisilazide and lithium dicyclohexylamide; and metal hydrides such as sodium hydride, potassium hydride and calcium hydride. These base can be used alone or as a mixture of two or more. The base may be selected in consideration of the type, the reactivity and the selectivity of a substrate.

The base may be used in amount of preferably 0.7 to 5 mol, more preferably 0.8 to 4 mol, even more preferably 0.9 to 3 mol relative to 1 mol of the phosphonium salt.

Examples of the solvent to be used in the Wittig reaction include ethers such as diethyl ether, dibutyl ether, tetrahydrofuran and 1,4-dioxane; hydrocarbons such as hexane, heptane, benzene, toluene, xylene and cumene; chlorinated solvents such as methylene chloride, chloroform and trichloroethylene; aprotic polar solvents such as N,N-dimethylformamide, 1,3-dimethyl-2-imidazolidinone, dimethyl sulfoxide and hexamethylphosphoric triamide; nitriles such as acetonitrile and propionitrile; esters such as ethyl acetate and n-butyl acetate; and alcohols such as methanol, ethanol and t-butyl alcohol. The solvent may be used alone or as a mixture of two or more. The solvent may be used in the Wittig reaction in an amount of preferably 10 to 10,000 g relative to 1 mol of the phosphonium salt.

A Wittig reaction at a lower reaction temperature results in higher Z-selectivity. The reaction temperature for the Wittig reaction may be preferably −78° C. to 30° C., more preferably −50° C. to 25° C., even more preferably −30° C. to 20° C. in consideration of workability and economic efficiency.

The reaction time of the Wittig reaction may be freely selected. The reaction time is preferably selected to complete the reaction by monitoring the reaction by gas chromatography (GC) or silica gel thin-layer chromatography (TLC) from the standpoint of yield. The reaction time is typically about 0.5 to about 24 hours.

[III] Method for Producing Terminal Conjugated Trienal Compound (2) Through Deprotection of Terminal Conjugated Trienal Acetal Compound (1)

The step of deprotecting the terminal conjugated trienal acetal compound represented by General Formula (1) to obtain a terminal conjugated trienal compound represented by General Formula (2) below will be described.

$$H_2C=CH-CH=CH-CH=CH-(CH_2)_n-CHO \quad (2)$$

As for the deprotection, an acid, optional water and an optional solvent are added to the substrate, and the deprotection reaction may be carried out with cooling or heating.

Examples of the acid to be used for the deprotection include inorganic acids such as hydrochloric acid, hydrobromic acid, hydroiodic acid, sulfuric acid, nitric acid and phosphoric acid, and salts thereof; organic acids such as formic acid, acetic acid, propionic acid, oxalic acid, trifluoroacetic acid, methanesulfonic acid, benzenesulfonic acid, p-toluenesulfonic acid and naphthalenesulfonic acid, and salts thereof; Lewis acids such as lithium tetrafluoroborate, boron trifluoride, boron trichloride, boron tribromide, aluminum trichloride, zinc chloride, zinc bromide, zinc iodide, tin tetrachloride, tin tetrabromide, tin dichloride, titanium tetrachloride, titanium tetrabromide and trimethyliodosilane; oxides such as alumina, silica gel and titania; and minerals such as montmorillonite. The acid may be used alone or as a mixture of two or more.

The acid is preferably used in a small amount from the standpoint of economic efficiency. The amount of the acid may be freely selected as long as a practically sufficient reaction rate is obtained. The amount thereof is preferably 0.00001 to 10,000 mol, more preferably 0.0001 to 1,000 mol, even more preferably 0.001 to 100 mol relative to 1 mol of the terminal conjugated trienal acetal compound as the substrate.

When the deprotection is carried out by hydrolysis, water is added for the reaction. A larger amount of water shifts the equilibrium to a direction of forming an aldehyde and thus is advantageous. The amount of water is preferably 1 to 10,000 mol, more preferably 1 to 1,000 mol, even more preferably 1 mol to 500 mol relative to 1 mol of the terminal conjugated trienal acetal compound as the substrate in consideration of economic efficiency, workability, yield and the like. The reaction may be carried out while removing an alcohol formed by the hydrolysis of the acetal from the system by distillation, phase separation or other techniques.

When irreversible deprotection is carried out, for example, by using a nucleophilic substitution reaction toward $R^1$ and $R^2$, water is not necessarily added.

Examples of the solvent to be used for the deprotection include ethers such as diethyl ether, dibutyl ether, tetrahydrofuran and 1,4-dioxane; hydrocarbons such as hexane, heptane, benzene, toluene, xylene and cumene; chlorinated solvents such as methylene chloride, chloroform and trichloroethylene; ketones such as acetone and 2-butanone; aprotic polar solvents such as N,N-dimethylformamide, 1,3-dimethyl-2-imidazolidinone, dimethyl sulfoxide and hexamethylphosphoric triamide; nitriles such as acetonitrile and propionitrile; esters such as ethyl acetate and n-butyl acetate; and alcohols such as methanol, ethanol and t-butyl alcohol. The solvent may be used alone or as a mixture of two or more. The solvent is used for the deprotection in an amount of preferable 10 to 10,000 g relative to 1 mol of the terminal conjugated trienal acetal compound.

When the deprotection is carried out by hydrolysis as described above, water may be used as the solvent. The water may be used in the above-described amount.

The reaction temperature of the deprotection varies depending on reaction conditions. The reaction temperature may be −78° C. to 160° C., preferably −50° C. to 140° C., more preferably −30° C. to 120° C.

The reaction time of the deprotection may be freely selected. The reaction time is preferably selected to complete the reaction by monitoring the reaction by gas chromatography (GC) or silica gel thin-layer chromatography (TLC) from the standpoint of yield. The reaction time is typically about 0.5 to about 24 hours.

The terminal conjugated trienal acetal compound represented by General Formula (1) can include four types of geometric isomers. When a (Z,E)-terminal conjugated trienal acetal compound represented by General Formula (3) is used as the substrate of the deprotection, a (Z,E)-terminal conjugated trienal compound represented by General Formula (4) can be produced.

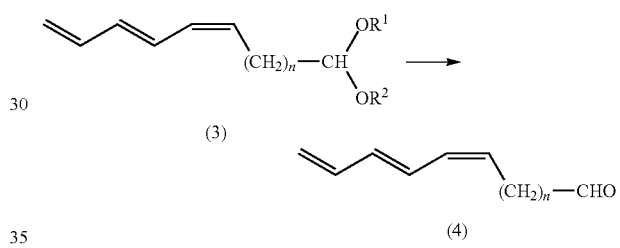

[IV] Enol Etherification of Terminal Conjugated Trienal Acetal Compound (1)

An acetal may produce an enol ether through elimination of one molecule of an alcohol by an acid or under a heating condition. The acetal and the enol ether can be converted into each other. The enol ether can be hydrolyzed to form a corresponding aldehyde in the same manner as the acetal. Enol ether compounds represented by General Formulae (1)′, (7)′, and (8)′ can also be used in the same manner as the terminal conjugated trienal acetal compound (1), the phosphonium salt (7) and the halide (8). In the general formulae, the definitions of n, $R^1$ and X are the same as above.

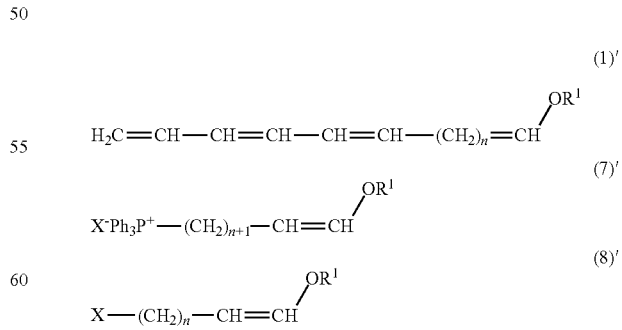

As described above, the simple and efficient method for producing a terminal conjugated trienal compound is provided to supply a sufficient amount of the product for application and utilization.

EXAMPLES

The present invention will next be described in further detail with reference to Examples. It should not be construed that the present invention is limited to or by them. The compound samples for spectrum measurement were obtained through optional purification of crude products.

Example 1

Production of (Z,E)-9,11,13-tetradecatrienal diethyl acetal

Under a nitrogen atmosphere, 9-chlorononanal diethyl acetal (225 g, 0.896 mol), triphenylphosphine (247 g, 0.941 mol), sodium iodide (148 g, 0.989 mol), potassium carbonate (6.2 g, 0.045 mol) and acetonitrile (540 g) were placed in a reaction vessel, and heated for reflux with stirring for 10 hours to obtain a phosphonium salt.

Into the same reaction vessel, THF (1,000 g) was added at room temperature, and then the mixture was stirred at 5° C. or less, subjected to addition of potassium t-butoxide (106 g, 0.941 mol), and stirred at 5° C. or less for 1 hour. Subsequently, a toluene solution of (E)-2,4-pentadienal (77.2 g, 0.941 mol) was added dropwise thereto at 10° C. or less, and the resulting mixture was stirred at 10° C. or less for 1 hour. Water was added to the reaction mixture, and the separated organic phase was subjected to common work-up including washing, drying and concentration. Then the precipitated triphenylphosphine oxide was removed by filtration, and the filtrate was concentrated to obtain a target (Z,E)-9,11,13-tetradecatrienal diethyl acetal (180 g, 0.641 mol) as a geometric isomer mixture of ZE:EE=87:14. Yield: 74%.

(Z,E)-9,11,13-Tetradecatrienal diethyl acetal

Colorless to Pale Yellow Oily Liquid

IR (D-ATR): ν=3016, 2974, 2927, 2855, 1438, 1374, 1345, 1120, 1062, 1004, 938, 897 cm$^{-1}$.

$^1$H-NMR (500 MHz, CDCl$_3$): δ=1.20 (6H, t, J=7.1 Hz), 1.27-1.40 (10H, m), 1.57-1.63 (2H, m), 2.18 (2H, dq, J=1.5, 7.7 Hz), 3.45-3.51 (2H, m), 3.60-3.66 (2H, m), 4.47 (1H, t, J=5.8 Hz), 5.07 (1H, d, J=10.7 Hz), 5.20 (1H, d, J=16.5 Hz), 5.47 (1H, dt, J=7.7, 10.7 Hz), 6.01 (1H, t, J=11.1 Hz), 6.19 (1H, dd, J=10.8, 15.0 Hz), 6.40 (1H, dt, J=10.3, 16.8 Hz), 6.49 (1H, dd, J=11.1, 14.9 Hz) ppm.

$^{13}$C-NMR (125 MHz, CDCl$_3$): δ=15.33, 24.71, 27.84, 29.14, 29.38, 29.58, 33.56, 60.78, 102.93, 116.80, 128.28, 128.65, 132.89, 133.51, 137.22 ppm.

GC-MS (EI, 70 eV): 29, 47, 65, 79, 103, 234, 280 (M$^+$).

Example 2

Production of (Z,E)-9,11,13-tetradecatrienal diethyl acetal

Under a nitrogen atmosphere, 9-chlorononanal diethyl acetal (133 g, 0.530 mol), triphenylphosphine (151 g, 0.575 mol), sodium bromide (79.0 g, 0.767 mol), potassium carbonate (3.8 g, 0.027 mol) and acetonitrile (534 g) were placed in a reaction vessel, and heated for reflux with stirring for 55 hours to obtain a phosphonium salt.

Into the same reaction vessel, THF (1,068 g) was added at room temperature, and then the mixture was stirred at 5° C. or less, subjected to addition of potassium t-butoxide (62.4 g, 0.556 mol), and stirred at 5° C. or less for 1 hour. Subsequently, a toluene solution of (E)-2,4-pentadienal (48.4 g, 0.589 mol) was added dropwise thereto at 10° C. or less, and the resulting mixture was stirred at 10° C. or less for 1 hour. Water was added to the reaction mixture, and the separated organic phase was subjected to common work-up including washing, drying and concentration. Then the precipitated triphenylphosphine oxide was removed by filtration, and the filtrate was concentrated to obtain a target (Z,E)-9,11,13-tetradecatrienal diethyl acetal (96.2 g, 0.343 mol) as a geometric isomer mixture of ZE:EE=87:14. Yield: 65%.

Example 3

Production of (Z,E)-9,11,13-tetradecatrienal diethyl acetal

Under a nitrogen atmosphere, 9-bromononanal diethyl acetal (23.1 g, 0.0784 mol), triphenylphosphine (23.9 g, 0.0910 mol), potassium carbonate (2.4 g, 0.017 mol) and acetonitrile (78 g) were placed in a reaction vessel, and heated for reflux with stirring for 25 hours to obtain a phosphonium salt.

Into the same reaction vessel, THF (163 g) was added at room temperature, and then the mixture was stirred at 5° C. or less, subjected to addition of potassium t-butoxide (10.7 g, 0.0954 mol), and stirred at 5° C. or less for 1 hour. Subsequently, a toluene solution of 2,4-pentadienal (7.12 g, 0.0867 mol) that was a geometric isomer mixture at E:Z=93:7 was added dropwise thereto at 10° C. or less, and the resulting mixture was stirred at 10° C. or less for 1 hour. Water was added to the reaction mixture, and the separated organic phase was subjected to common work-up including washing, drying and concentration. Then the precipitated triphenylphosphine oxide was removed by filtration, and the filtrate was concentrated to obtain a target (Z,E)-9,11,13-tetradecatrienal diethyl acetal (96.2 g, 0.343 mol) as a geometric isomer mixture of ZE:EE:(EZ+ZZ)=83:12:5. Yield: 65%.

Example 4

Production of (Z,E)-9,11,13-tetradecatrienal ethylene acetal

The same procedure as in Example 1 was carried out except that 9-chlorononanal ethylene acetal (198 g, 0.896 mol) was used in place of 9-chlorononanal diethyl acetal (225 g, 0.896 mol), to obtain (Z,E)-9,11,13-tetradecatrienal ethylene acetal (160 g, 0.641 mol) as a geometric isomer mixture of ZE:EE=87:14. Yield: 74%.

(Z,E)-9,11,13-Tetradecatrienal ethylene acetal

Colorless to Pale Yellow Oily Liquid

IR (D-ATR): ν=3016, 2926, 2855, 1435, 1139, 1036, 1005, 942, 897 cm$^{-1}$.

$^1$H-NMR (500 MHz, CDCl$_3$): δ=1.25-1.43 (10H, m), 1.62-1.67 (2H, m), 2.16-2.20 (2H, m), 3.80-3.87 (2H, m), 3.92-3.99 (2H, m), 4.83 (1H, t, J=5.0 Hz), 5.07 (1H, d, J=9.9 Hz), 5.20 (1H, d, J=16.4 Hz), 5.47 (1H, dt, J=7.7, 11.1 Hz), 6.00 (1H, t, J=11.1 Hz), 6.19 (1H, dd, J=10.5, 14.6 Hz), 6.40 (1H, dt, J=10.7, 16.8 Hz), 6.49 (1H, dd, J=11.5, 14.9 Hz) ppm.

$^{13}$C-NMR (125 MHz, CDCl$_3$): δ=24.01, 27.83, 29.08, 29.44, 29.48, 30.28, 33.88, 64.78, 104.64, 116.79, 128.26, 128.64, 132.88, 133.51, 137.21 ppm.

Example 5

Production of (Z,E)-9,11,13-tetradecatrienal

Under a nitrogen atmosphere, the geometric isomer mixture of (Z,E)-9,11,13-tetradecatrienal diethyl acetal (482 g, 1.72 mol) produced by the method of Example 1, THF (1,000 g), water (2,500 g) and p-toluenesulfonic acid monohydrate (12.4 g, 0.0653 mol) were placed in a reaction vessel, and heated for reflux with stirring for 10 hours. The organic phase separated from the reaction mixture was subjected to common work-up including washing, drying and concentration. The concentrated solution obtained was distilled under vacuum to obtain a target (Z,E)-9,11,13-tetradecatrienal (248 g, 1.20 mol) as a geometric isomer mixture of ZE:EE=87:13. Yield: 70%. No change in the ratio of the geometric isomers was observed before and after the reaction.

(Z,E)-9,11,13-Tetradecatrienal

Colorless to Pale Yellow Oily Liquid

Boiling point: 115-136° C./2 mmHg

IR (D-ATR): ν=3016, 2928, 2855, 2718, 1725, 1622, 1577, 1464, 1391, 1005, 940, 897 cm$^{-1}$.

$^1$H-NMR (500 MHz, CDCl$_3$): δ=1.31-1.40 (8H, m), 1.58-1.63 (2H, m), 2.16-2.21 (2H, m), 2.41 (2H, dt, J=1.9, 7.5 Hz), 5.07 (1H, d, J=9.9 Hz), 5.20 (1H, d, J=16.8 Hz), 5.46 (1H, dt, J=7.7, 10.7 Hz), 6.01 (1H, t, J=10.7 Hz), 6.20 (1H, dd, J=10.7, 14.9 Hz), 6.40 (1H, dt, J=10.7, 16.8 Hz), 6.49 (1H, dd, J=11.1, 14.9 Hz), 9.75 (1H, t, J=1.7 Hz) ppm.

$^{13}$C-NMR (125 MHz, CDCl$_3$): δ=22.00, 27.77, 28.95, 29.05, 29.16, 29.48, 43.85, 116.89, 128.36, 128.58, 132.96, 133.34, 137.17, 202.83 ppm.

GC-MS (EI, 70 eV): 29, 41, 55, 67, 79, 91, 107, 206 (M$^+$).

Example 6

Production of (Z,E)-9,11,13-tetradecatrienal

Under a nitrogen atmosphere, the geometric isomer mixture of (Z,E)-9,11,13-tetradecatrienal diethyl acetal (18.3 g, 0.0651 mol) produced by the method of Example 3, THF (50 g), water (125 g) and p-toluenesulfonic acid monohydrate (0.54 g, 0.0028 mol) were placed in a reaction vessel, and heated for reflux with stirring for 9 hours. The organic phase separated from the reaction mixture was subjected to common work-up including washing, drying and concentration. The concentrated solution obtained was distilled under vacuum to obtain a target (Z,E)-9,11,13-tetradecatrienal (8.80 g, 0.0314 mol) as a geometric isomer mixture of ZE:EE:(EZ+ZZ)=83:12:5. Yield: 48%. No change in the ratio of the geometric isomers was observed before and after the reaction.

Example 7

Production of (Z,E)-9,11,13-tetradecatrienal

Under a nitrogen atmosphere, the geometric isomer mixture of (Z,E)-9,11,13-tetradecatrienal diethyl acetal (0.925 g, 0.00330 mol) produced by the method of Example 1, THF (22 g), water (11 g) and oxalic acid dihydrate (0.20 g, 0.0016 mol) were placed in a reaction vessel, and heated for reflux with stirring for 10 hours. The organic phase separated from the reaction mixture was subjected to common work-up including washing, drying and concentration. The concentrated solution obtained was purified by silica gel column chromatography to obtain a target (Z,E)-9,11,13-tetradecatrienal (0.640 g, 0.00310 mol) as a geometric isomer mixture of ZE:EE=87:13. Yield: 94%. No change in the ratio of the geometric isomers was observed before and after the reaction.

Example 8

Production of (Z,E)-9,11,13-tetradecatrienal

Under a nitrogen atmosphere, the geometric isomer mixture of (Z,E)-9,11,13-tetradecatrienal ethylene acetal (4.2 g, 0.012 mol) produced by the method of Example 4, THF (53 g), water (126 g) and p-toluenesulfonic acid monohydrate (0.65 g, 0.0034 mol) were placed in a reaction vessel, and heated for reflux with stirring for 15 hours. The organic phase separated from the reaction mixture was subjected to common work-up including washing, drying and concentration. The concentrated solution obtained was purified by silica gel column chromatography to obtain a target (Z,E)-9,11,13-tetradecatrienal (2.3 g, 0.011 mol) as a geometric isomer mixture of ZE:EE=87:13. Yield: 92%. No change in the ratio of the geometric isomers was observed before and after the reaction.

The invention claimed is:

1. A terminal conjugated trienal acetal compound of General Formula (1):

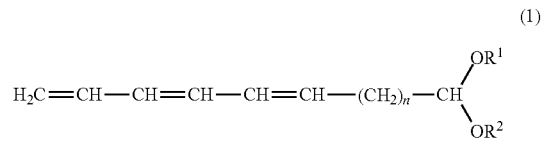

wherein n is an integer of 2 to 11; and each of R$^1$ and R$^2$ independently is a monovalent hydrocarbon group having 1 to 10 carbon atoms, or R$^1$ and R$^2$ are bonded to each other to form a divalent hydrocarbon group having 2 to 10 carbon atoms as R$^1$-R$^2$.

2. The terminal conjugated trienal acetal compound according to claim 1, wherein the terminal conjugated trienal acetal compound is a (Z,E)-terminal conjugated trienal acetal compound of General Formula (3):

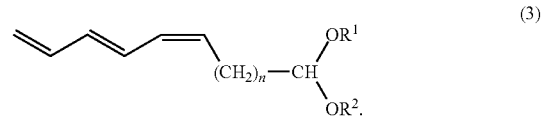

3. The terminal conjugated trienal acetal compound according to claim 1, wherein the terminal conjugated trienal acetal compound is a (Z,E)-9,11,13-tetradecatrienal acetal compound of General Formula (5):

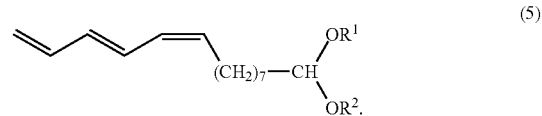

4. A method for producing a (Z,E)-terminal conjugated trienal acetal compound, the method comprising the step of:
reacting a phosphonium salt of General Formula (7):

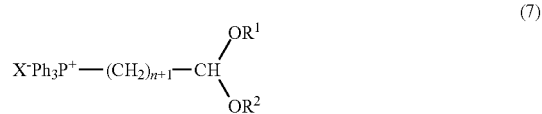

wherein n is an integer of 2 to 11; each of R$^1$ and R$^2$ independently is a monovalent hydrocarbon group having 1 to 10 carbon atoms, or R$^1$ and R$^2$ are bonded to each other to form a divalent hydrocarbon group having 2 to 10 carbon atoms as R$^1$-R$^2$; and X is a halogen atom, with (E)-2,4-pentadienal through a Wittig reaction to obtain a (Z,E)-terminal conjugated trienal acetal compound represented by General Formula (3):

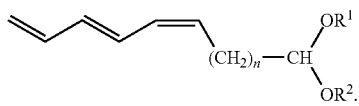
(3)

5. A method for producing a terminal conjugated trienal compound, the method comprising the step of:
deprotecting a terminal conjugated trienal acetal compound of General Formula (1):

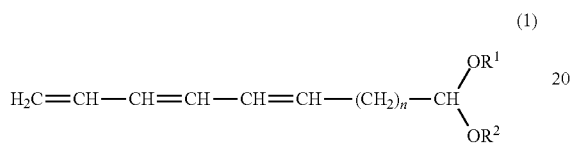
(1)

wherein n is an integer of 2 to 11; and each of $R^1$ and $R^2$ independently is a monovalent hydrocarbon group having 1 to 10 carbon atoms, or $R^1$ and $R^2$ are bonded to each other to form a divalent hydrocarbon group having 2 to 10 carbon atoms as $R^1$-$R^2$, to obtain a terminal conjugated trienal compound of General Formula (2):

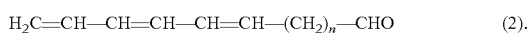
(2).

6. The method for producing a terminal conjugated trienal compound according to claim 5, wherein the terminal of compound is a (Z,E)-terminal conjugated trienal acetal compound represented by General Formula (3):

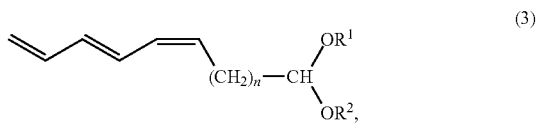
(3)

and the terminal conjugated trienal compound is a (Z,E)-terminal conjugated trienal compound of General Formula (4):

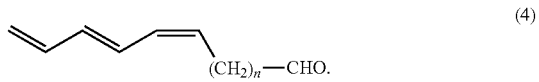
(4)

* * * * *